United States Patent
Zoeller, III

(10) Patent No.: US 8,285,027 B2
(45) Date of Patent: Oct. 9, 2012

(54) HIGH-RESOLUTION LARGE-FIELD SCANNING INSPECTION SYSTEM FOR EXTRUDED CERAMIC HONEYCOMB STRUCTURES

(75) Inventor: Leon Robert Zoeller, III, Hammondsport, NY (US)

(73) Assignee: Corning Incorporated, Corning, NY (US)

( * ) Notice: Subject to any disclaimer, the term of this patent is extended or adjusted under 35 U.S.C. 154(b) by 544 days.

(21) Appl. No.: 12/617,778

(22) Filed: Nov. 13, 2009

(65) Prior Publication Data

US 2011/0116704 A1    May 19, 2011

(51) Int. Cl.
*G06K 9/00* (2006.01)
(52) U.S. Cl. .................................................. 382/141
(58) Field of Classification Search .................. 382/141
See application file for complete search history.

(56) References Cited

U.S. PATENT DOCUMENTS

| | | | |
|---|---|---|---|
| 3,826,923 A | 7/1974 | Trimble et al. | |
| 4,319,840 A | 3/1982 | Kondo et al. | |
| 6,605,807 B2 | 8/2003 | Safai | |
| 6,862,089 B2 * | 3/2005 | Goto et al. | 356/237.6 |
| 6,906,795 B2 * | 6/2005 | Goto et al. | 356/237.6 |
| 7,043,998 B2 | 5/2006 | Werve | |
| 7,283,224 B1 * | 10/2007 | Smithgall | 356/237.1 |
| 8,000,516 B2 * | 8/2011 | Ito et al. | 382/141 |
| 8,049,878 B2 * | 11/2011 | Zoeller, III | 356/237.6 |
| 2002/0051563 A1 * | 5/2002 | Goto et al. | 382/141 |
| 2002/0109837 A1 * | 8/2002 | Goto et al. | 356/237.6 |
| 2008/0115597 A1 | 5/2008 | Ohno et al. | |
| 2010/0045975 A1 * | 2/2010 | Zoeller, III | 356/239.2 |

FOREIGN PATENT DOCUMENTS

| | | |
|---|---|---|
| EP | 2 006 666 | 12/2008 |
| JP | 2002-257736 | 9/2002 |
| JP | 2002-267427 | 9/2002 |
| WO | 2007/070318 | 6/2007 |
| WO | 2007/126692 | 4/2008 |

* cited by examiner

*Primary Examiner* — Roy M Punnoose
(74) *Attorney, Agent, or Firm* — Matthew J. Mason; Joseph Gortych

(57) ABSTRACT

A high-resolution, large-field scanning inspection system for inspecting extruded ceramic honeycomb structures is disclosed. The system allows for inspecting cells at an endface of a cellular ceramic substrate by capturing, along an optical axis, line images of illuminated cells as a line illumination scans over at least a portion of the plurality of cells. The inspection method includes centering the line illumination on the optical axis to make the line illumination normally incident upon the endface. The inspection method also includes forming from the line images a composite image of the cells, and determining from the composite image at least one parameter of at least one cell.

20 Claims, 13 Drawing Sheets

US 8,285,027 B2

HIGH-RESOLUTION LARGE-FIELD SCANNING INSPECTION SYSTEM FOR EXTRUDED CERAMIC HONEYCOMB STRUCTURES

FIELD

This disclosure generally relates to systems and methods for inspecting structures, and in particular to a high-resolution scanning inspection system for inspecting extruded ceramic honeycomb structures.

BACKGROUND

Ceramic honeycomb structures are used in vehicular exhaust systems to reduce pollutants. Such structures are generally formed by extrusion and comprise a network of interconnected web walls that form a matrix of elongated, gas-conducting cells which may be square, octagonal or hexagonal in shape, for example. The network of web walls is surrounded by a cylindrical outer skin that is integrally connected to the outer edges of the web walls to form a cylindrical structure having opposing inlet and outlet endfaces for receiving and expelling exhaust gases through the matrix of cells.

Such ceramic honeycomb structures need to be inspected to ensure they meet specifications for cell shape, cell size, web-wall thickness, skin integrity, etc., and to ensure they are free of defects. However, given the large numbers of cells (typically, many thousands) and the diameter of such structures (typically 3.5" to 7.5"), it usually takes many hours to inspect a single ceramic honeycomb structure using conventional inspection methods and systems.

Consequently, improved inspection systems and methods that can quickly and efficiently inspecting ceramic honeycomb structures are needed.

SUMMARY

An aspect of the present disclosure is an inspection system for inspecting cells of a cellular ceramic substrate. The system includes an illuminator configured to provide normal-incidence line illumination on the endface over a plurality of cells. The system also has a movable stage that movably supports the ceramic structure so that the line illumination scans over the endface over a scan path. The system further includes an optical imaging system having an axis and configured to form a line image of the illuminated plurality of cells. The system also has a line-scan image sensor arranged to receive and detect the line image and generate therefrom corresponding line-image signals. The system further includes a controller configured to process the line-image signals to form a composite image of the endface and determine therefrom at least one parameter of at least one cell.

Another aspect of the present disclosure is a method of inspecting cells at an endface of a cellular ceramic substrate. The method includes capturing, along an optical axis, line images of illuminated cells as a line illumination scans over at least a portion of the plurality of cells, including centering the line illumination on the optical axis to make the line illumination normally incident upon the endface. The method also includes forming from the line images a composite image of the cells. The method further includes determining from the composite image at least one parameter of at least one cell.

Another aspect of the present disclosure is a method of inspecting a honeycomb cellular ceramic substrate having an endface, an array of cells and an outer skin. The method includes normally illuminating and digitally imaging at least a portion of the array of cells while moving the cellular ceramic structure to obtain a scanned image of the portion of the array of cells. The method also includes processing the scanned image to determine at least one parameter of at least one cell.

It is to be understood that both the foregoing general description and the following detailed description present embodiments of the disclosure, and are intended to provide an overview or framework for understanding the nature and character of the disclosure as it is claimed. The accompanying drawings are included to provide a further understanding of the disclosure, and are incorporated into and constitute a part of this specification. The drawings illustrate various embodiments of the disclosure and, together with the description, serve to explain the principles and operations of the disclosure.

DETAILED DESCRIPTION

Reference is now made in detail to the present preferred embodiments of the disclosure, examples of which are illustrated in the accompanying drawings. Whenever possible, the same or analogous reference numbers are used throughout the drawings to refer to the same or like parts.

Ceramic Honeycomb Structures

Figure 1:
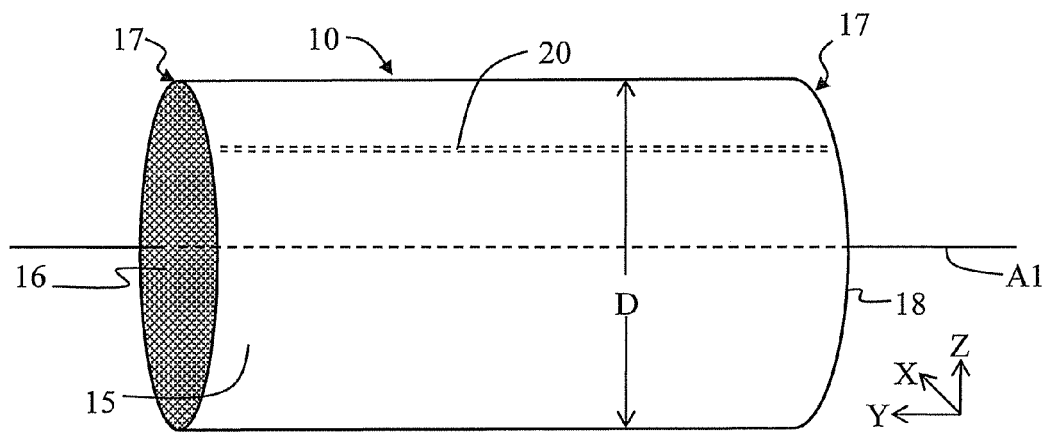
FIG. 1 is an isometric view of an example ceramic honeycomb structure.
Figure 2:
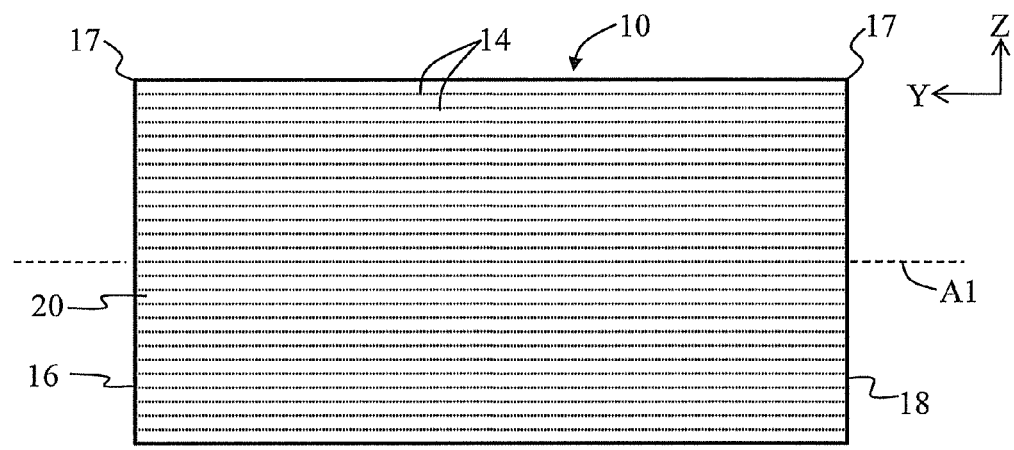
FIG. 2 is a side view of the ceramic honeycomb structure of FIG. 1.
Figure 3:
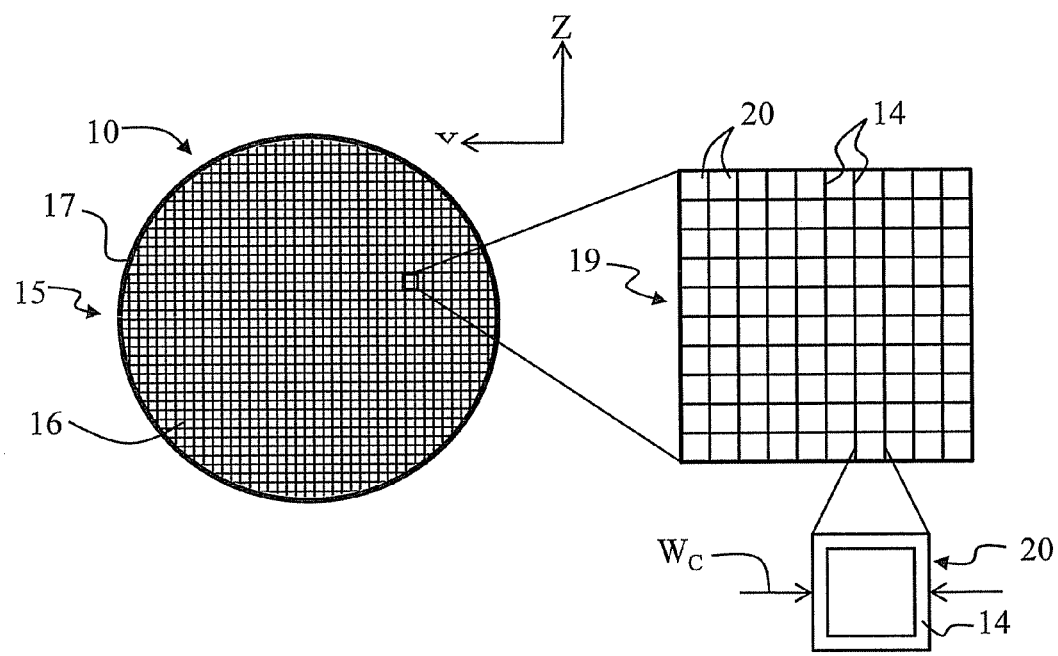
FIG. 3 is an end-on view of the ceramic honeycomb structure of FIG. 1 that includes a close-up view of an example matrix of square cells.

FIG. 1 is an isometric view of an example ceramic honeycomb structure 10. FIG. 2 is a side view of the ceramic honeycomb structure 10 of FIG. 1, and FIG. 3 is an end-on view that includes a close-up view shown in the inset. Cartesian X-Y-Z coordinates are shown for the sake of reference. Ceramic honeycomb structure 10 has a central axis A1 that defines an axial (longitudinal) direction. Ceramic honeycomb structure includes a matrix of intersecting, thin, porous walls 14 surrounded by an outer skin 15. Walls 14 extend across and between opposing endfaces 16 and 18, and form a large number of adjoining hollow passages or "cells" 20 that also extend between, and are open at, the endfaces. Outer skin 15 has a perimeter 17 at each end face 16 and 18. The intersecting walls 14 at end faces 16 and 18 form a "web" 19, and walls 14 constitute "web walls" or "cell walls."

In an example embodiment, ceramic honeycomb structure 10 as used to form a flow-through catalyst filter has, for example, between 100 to 900 cells per square inch, which translates into a cell width $W_C$ (FIG. 3) that can range from between about 2.5 mm to about 0.85 mm. Walls 14 of such a ceramic body 10 can be rendered quite thin, e.g., on the order of 2-10 mils thick, or even 2-6 mils thick. Other filter types (e.g., smoke-stack filters) utilize ceramic honeycomb structures 10 having on the order of 50 cells per square inch, which translates into a cell width of about 3.6 mm. Other types of filters can have higher cell densities, e.g., thousands of cells per square inch.

In some applications, ceramic honeycomb structures 10 are used as flow-through catalyst substrates have cells 20 that are completely open between endfaces 16 and 18. Cell density may be maximized in order to maximize the area of contact between the automotive exhaust gases that flow directly through gas-conducting cell 20 and walls 14. To reduce the pressure drop that the flow-through catalyst imposes on the exhaust gases, walls 14 can be rendered quite thin, i.e. on the order of 2-10 mils, or even 2-6 mils.

When ceramic honeycomb structures 10 are used as wall-flow filters, such as diesel particulate filters, the open ends of cells 20 at the inlet and outlet endfaces 16 and 18 are plugged, for example, in a "checkerboard" pattern, to force the exhaust gases to pass through the porous walls 14 before exiting endface 18. The density of cells 20 is lower than for catalytic converters, e.g., typically between about 100 and 400 cells per square inch. Further, walls 14 can be generally thicker, on the order of 10-25 mils thick, or even 12-16 mils thick, for example. Whether ceramic honeycomb structures 10 are used as a catalytic carrier or a particulate filter, the outer skin 15 can be about four times as thick as walls 14.

Ceramic honeycomb structures 10 are manufactured by extruding a plasticized ceramic-forming precursor, e.g., precursors of of cordierite, mullite, silicon carbide or aluminum titanate, through an extrusion die. The extruded "green body" is then cut and dried. Such green bodies are quite fragile, and are transported to a kiln, where the resultant heat transforms the relatively soft and fragile green body into a hardened, fired porous honeycomb structure.

During the manufacturing process, defects might occur in ceramic honeycomb structure 10. Such defects include, for example, wall thickness variations within the interior of the structure, wall orientation and/or waviness, cell shape variations and like geometrical deformities, skin thickness variations, and skin delamination. The defects also include microstructural variations, such as density differences and cracks. These defects impact the structural integrity of ceramic honeycomb structure 10 and influence the performance of the particular device formed from the structure.

Inspection System

Figure 4:
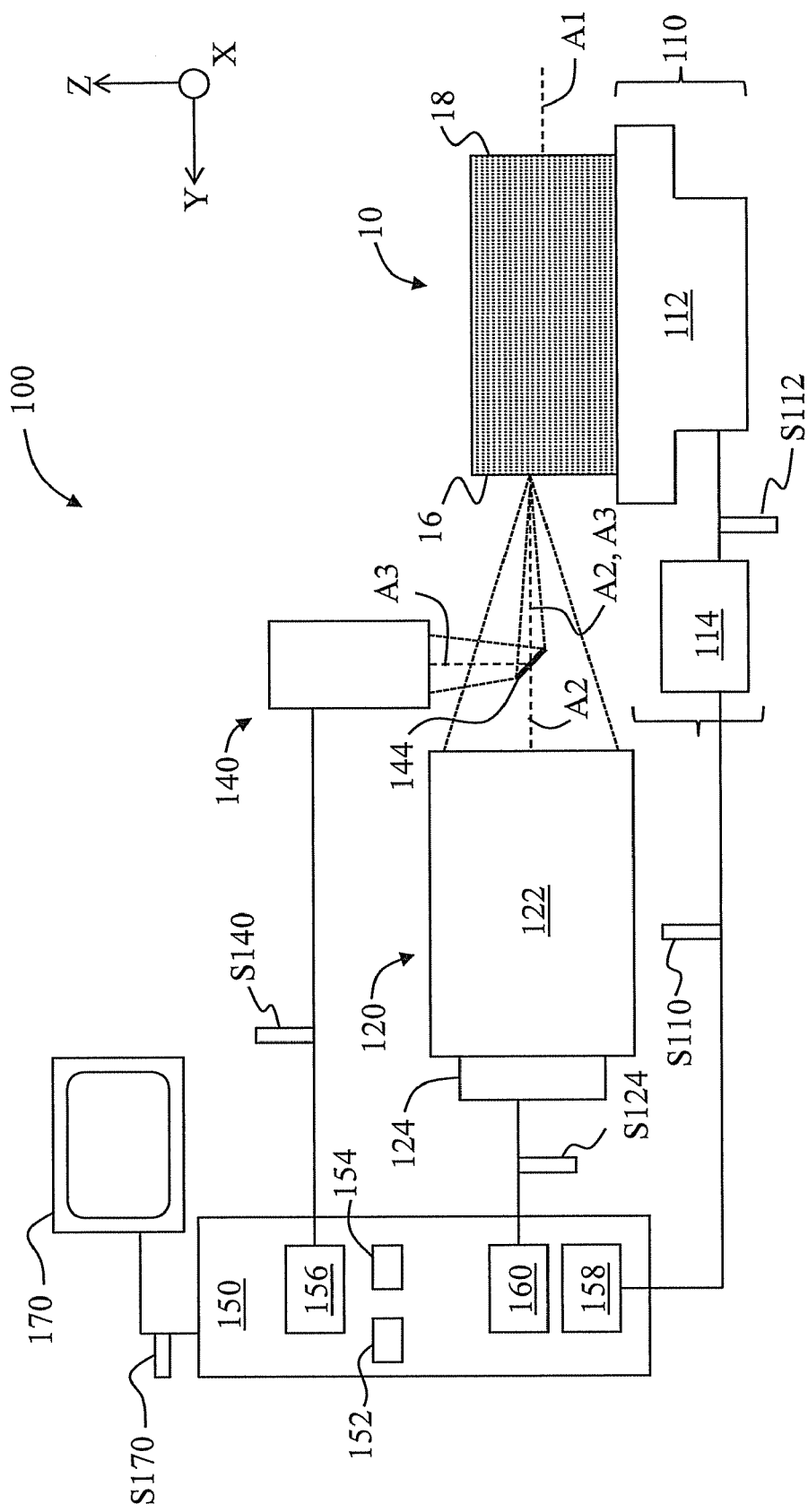
FIG. 4 is a schematic diagram of an example embodiment of a high-resolution large-field scanning system for inspecting the ceramic honeycomb structure shown in FIG. 1.

FIG. 4 is a schematic diagram of an example embodiment of a high-resolution large-field scanning inspection system ("system") 100 for inspecting a ceramic honeycomb structure 10, which is shown arranged within the system. System 100 includes a three-axis transport system 110 having a stage 112 configured to support ceramic honeycomb structure 10 so that endface 16 lies in the X-Z plane. Transport system 110 includes a stage driver 114 operably connected to stage 112 and that drives the stage to move the structure in three dimensions with a very high degree of precision (i.e., micron level) while maintaining enface 16 in a particular X-Z plane.

System 100 also includes an imaging optical system 120 having an optical axis A2, an imaging lens 122 with object and image planes OP and IP (FIG. 5) and a line-scan image sensor 124. Imaging optical system 120 is arranged relative to ceramic honeycomb structure 10 so that optical axis A1 is parallel to ceramic honeycomb structure axis A1. Imaging optical system 120 is configured so that imaging lens 122 images a line portion of endface 16 covering a plurality of cells 20 onto line-scan image sensor 124.

System 100 also includes an illumination system 140 having an axis A3 and that is configured to form normal-incident illumination of the aforementioned imaged line portion on endface 16. Illumination system 140 includes a fold-mirror 144 that serves to co-align illumination system axis A3 with optical system axis A2.

System 100 also includes a controller 150 operably connected to transport system 110, to optical system 120 and to illumination system 140, and that is configured to control the scanning process as described below. Controller 150 is or includes a computer, such as a workstation, that includes a processor unit 152 having one or more processors with image-processing capability (e.g., image-processing software) embodied in a computer-readable medium such as a memory unit 154. Memory unit 154 can be any of the know types of memory used for storing information for use by computers or processors, including solid-state memory or optical-disk memory. An example image-processing and image analysis software is the WiT software package from Dalsa Digital Imaging Co., Burnaby BC, Canada. Controller 150 also includes an illuminator system interface 156 operably connected to illuminator 140, a transport system interface 158 operably connected to transport system 110, and an image-sensor interface 160 operably connected to line-scan image sensor 124.

System 100 further includes a display unit 170 connected to controller 150 and configured to display numeric, alphanumeric, and graphical information of the type discussed in detail below.

Figure 5:
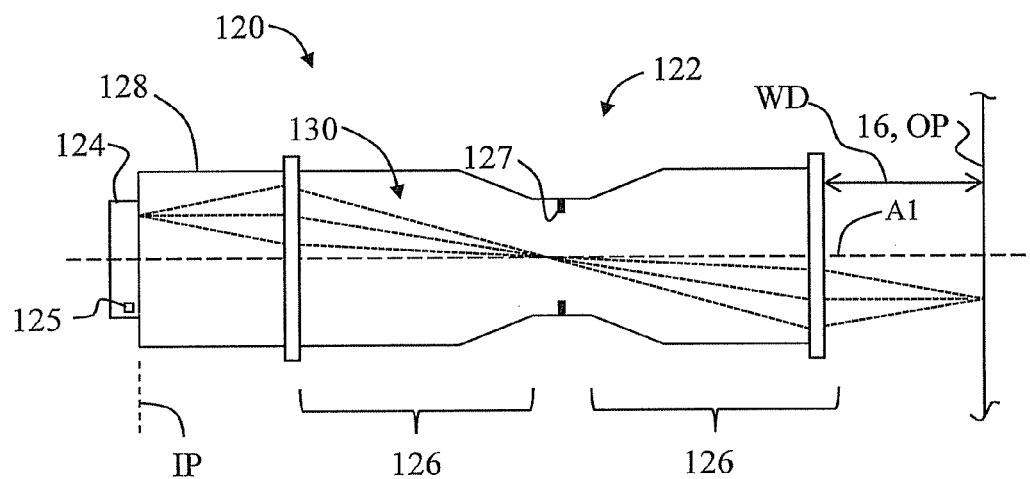
FIG. 5 is a schematic diagram of an example imaging optical system that includes a double-telecentric imaging lens, for use in the high-resolution large-field scanning system of FIG. 4.

FIG. 5 is a schematic diagram of an example imaging optical system 120. The example imaging optical system 120 includes a double-telecentric imaging lens 122. In the example shown in FIG. 5, imaging lens 122 is formed from two identical telecentric lenses 126 arranged back to back with an iris 127 in between to form a doubly telecentric 1:1 imaging system. Example telecentric lenses 126 are available, for example, from Sill Optics GmbH & Co., Wendelstein, Germany. An example light-ray path 130 between the object and image planes OP and IP is shown in phantom by way of illustration. In an example embodiment, imaging lens 122 has a depth-of-focus of about +/−100 μm, which allows for imaging endface 16 without having to re-focus imaging lens 122. A lens barrel portion 128 connects two identical telecentric lenses 126 with line-scan image sensor 124. An example imaging lens 121 has a 4 inch aperture, an 8 inch working distance WD, and images an object field of about 4 inches at an object plane OP, which is maintained coincident with endface 16 of ceramic honeycomb structure 10. The 1:1 imaging forms an image that is about 2.3 inches long on line-scan image sensor 124, which in an example embodiment includes 1×12K array of 5 μm by pixels 5 μm that has a length of about 2.4 inches. In another example embodiment, line-scan image sensor 124 includes at least about 8,000 square pixels having sides of less than or equal to about 5 μm. The scanned image, obtained as described below, has a "width" of about 6 inches. Optical intensity is measured using a 12-bit converter.

Figure 6:
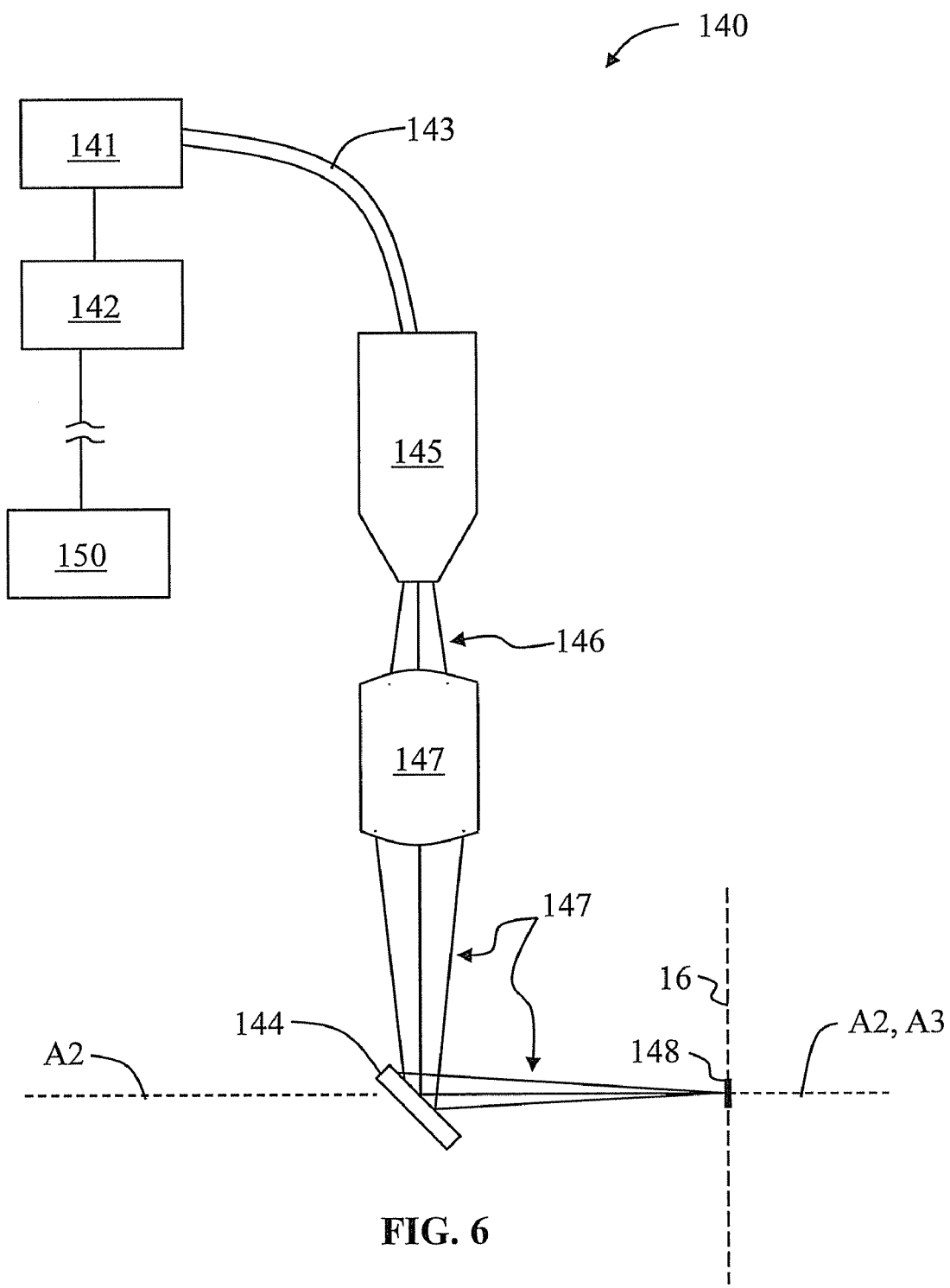
FIG. 6 is a schematic diagram of an example illumination system for use in the high-resolution large-field scanning system of FIG. 4.

FIG. 6 is a schematic diagram of an example illumination system 140 that includes a light source 141 and power supply unit 142, which connects to controller 150. An example light source 141 is or includes a metal-halide lamp. Light source 141 is optically connected via a flexible fiber optic bundle 143 to a light-line generator 145 that generates a line light beam 146. In an example embodiment, light line beam 146 forms a line of light about 3 inches in length. A cylindrical lens 147 is arranged adjacent the output end of light-line generator 145 and is configured to focus line light beam 146 to form a focused line beam 147 that forms line illumination 148 at endface 16. Here, "line illumination" means illumination having an elongate shape. In an example embodiment, line illumination 148 has a generally rectangular form, with one example size being 3 inches by 0.125 inches.

Fold mirror 144 serves to fold axis A3 so that it is co-aligned with optical system axis A2. The causes focused line beam 147 to be reflected along axis A2 and be normally incident upon endface 16. In an example embodiment, fold mirror 144 is about 0.5 inch wide and 4 inches in length (in the X-direction), so that when it is arranged at a 45° angle relative to axis A2 to provide a 90° reflection, it has an effective on-axis width of about 0.35 inches. Fold mirror 144 thus presents a thin-strip obscuration of imaging lens 122 that only minimally effects light collection and imaging performance.

Normally incident illumination formed by focused line beam 148 is preferred when seeking to acquire a true image of cells 20 and cell walls 14 at endface 16. For illumination that is incident endface 16 at an angle other than normal, the light reflects off of the side of walls 14, thereby producing flair that tends to make the walls to appear wider than they really are.

Scanned Image Acquisition & Composite Image Formation

With reference again to FIG. 4, in the operation of system 100 to acquire a scanned image of endface 16, controller 150 sends a signal S140 to illumination system 140 to turn on light source 141 via the operation of power supply 142. Obtaining a scanned image of endface 16 is carried out by either moving imaging optical system 120 relative to the ceramic honeycomb structure 10 or by moving the ceramic honeycomb structure relative to the imaging optical system. System 100 as shown in FIG. 4 is configured by way of example to move the ceramic honeycomb structure 10 relative to imaging optical system 120. Thus, controller 150 sends a transport control signal S110 to transport control system 110 to cause the stage driver 114 to move stage 112 so that endface 16 moves past imaging lens 122 at a constant velocity while substantially maintaining the endface in a X-Z plane, i.e., to within the depth of field of the imaging lens.

The width of the image formed is defined by the pixel width of line-scan image sensor 124. The pixel size in the scan direction is determined by the scan speed of ceramic honeycomb structure 10 and the scan rate of line-scan image sensor 124. For example, if the scan speed of ceramic honeycomb structure 10 is 1 cm/s and the scan rate of the line-scan camera is 200 scans per second, then the pixel size in the scan direction would be 5 μm. The typical CCD-based image sensor scans at a rate between 20,000 and 40,000 scans per second. For scanning at 20,000 scans per second, ceramic honeycomb structure 10 would need to be moved at scan speed of 100 cm/s, which is a very high rate of speed and would require significant acceleration and deceleration. This also means that illuminator system 140 would need to provide very bright illumination to maintain a useful exposure, since the effective exposure time for such high scan speeds would be 1/20,000 of a second.

While system 100 is capable of very fast scan speeds, more realistic illumination and exposure conditions and stage-movement conditions call for example scan speeds of between 5 cm/s to 10 cm/s. For scanning at varying scan speeds, in an example embodiment the scan speed of ceramic honeycomb structure 10 is linked to a scan rate (i.e., scan clock rate) of line-scan image sensor 124 by an encoder 125 (FIG. 5) so that system 100 consistently produces a 5 μm image width in the scan direction. This allows system 100 to scan slower if more light is needed (e.g., for a dark ceramic honeycomb structure) and to scan faster when less light is needed (e.g., for a light ceramic honeycomb structure).

Figure 7:
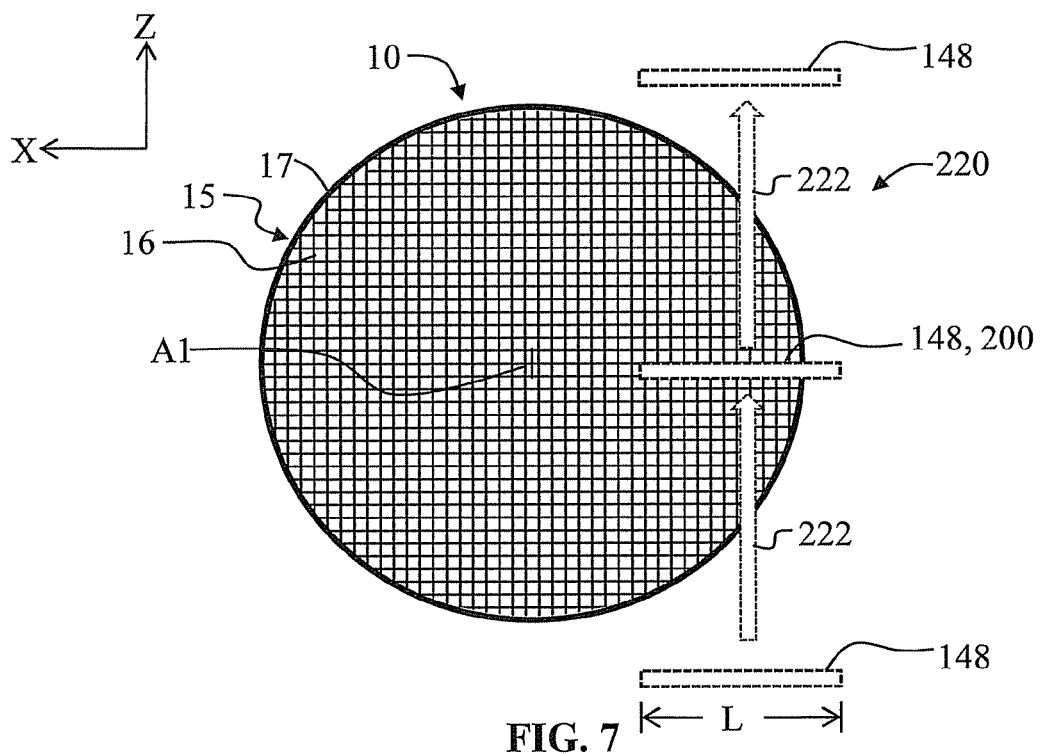
FIG. 7 is an end-on view of the ceramic honeycomb structure endface illustrating how the normally incident focused line beam illuminates a line portion of web as it travels over a scan path.
Figure 8:
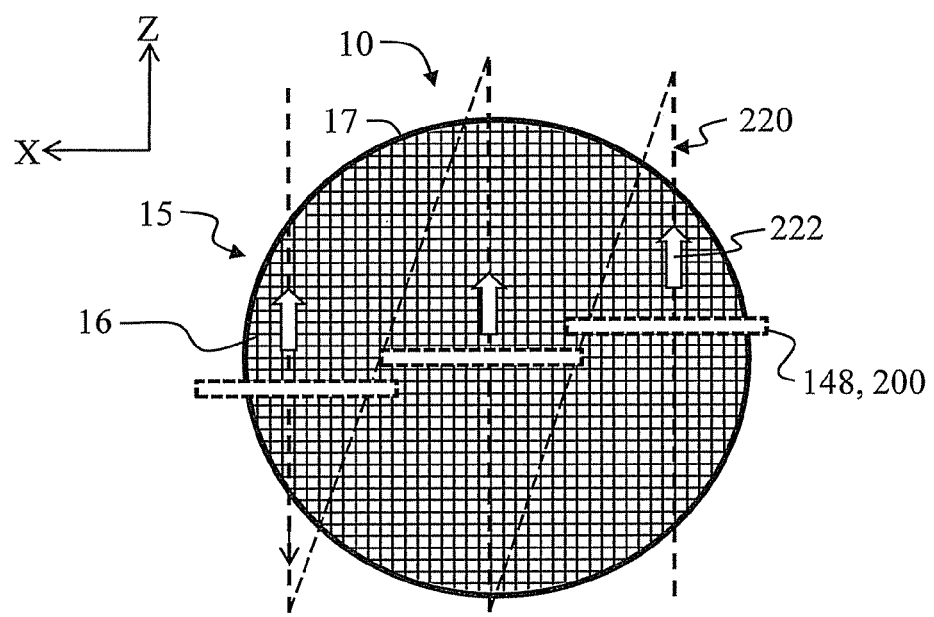
FIG. 8 is similar to FIG. 7 and shows an example scan path for the illuminated line portion as the ceramic honeycomb structure is translated by the transport system that supports the ceramic honeycomb structure.

With reference also to FIG. 7, normally incident focused line beam 147 forms line illumination 148 that illuminates a corresponding line portion 200 of web 19 of endface 16. Illuminated line portion 200 covers a plurality of cells 20. The light reflects off of illuminated portion 200 of web 19 and is imaged by imaging lens 122 onto line-scan image sensor 124, which captures a digital line image. In an example embodiment, illuminated line portion 200 has a length L of about 2.4 inches so that the corresponding the image formed on line-scan image sensor 124 is also about 2.4 inches. An example scan speed is about 2.5 cm/s (i.e., 1 inch/s), and an example image-capture speed is about two to three minutes. The scan path 220 of line illumination 148 is indicated by arrows 222. FIG. 8 is similar to FIG. 7 and illustrates an example scan path 220 of line illumination 148 over endface 16, with no imaging taking place over the diagonal sections of the scan path.

In an example embodiment, the captured digital line images are transferred to controller memory unit 154 via an image-sensor signal S124 from line-scan image sensor 124. In those cases where endface 16 has a diameter greater than the length of illuminated portion 200 illuminated by line illumination 148, multiple scans across endface 16 are used to capture a scanned image of the entire endface 16, as shown in FIG. 8. In an example embodiment, the scanned digital images of adjacent scan path segments include some overlap so that they the images can be stitched together to form a digital composite image of endface 16. In an example embodiment, the scan is carried out so that outer skin 15 is included in the scanned image so that the outer skin can be examined and also provide edge information that assists in defining relative positions in the captured scanned images for multiple scanned images. An image of outer skin 15 also provides information about the overall cross-sectional shape and the geometric center of ceramic honeycomb structure 10.

In a typical inspection, two or more scans generate corresponding two or more captured scan images each covering a portion of ceramic honeycomb structure endface 16. The scanned images are combined to form a composite scanned image of the entire endface 16. In an example embodiment, the composite scanned image is formed by performing an autocorrelation with adjacent scanned images, where the adjacent images include the aforementioned overlapping portion (e.g., of a few hundred pixels).

Figure 9:
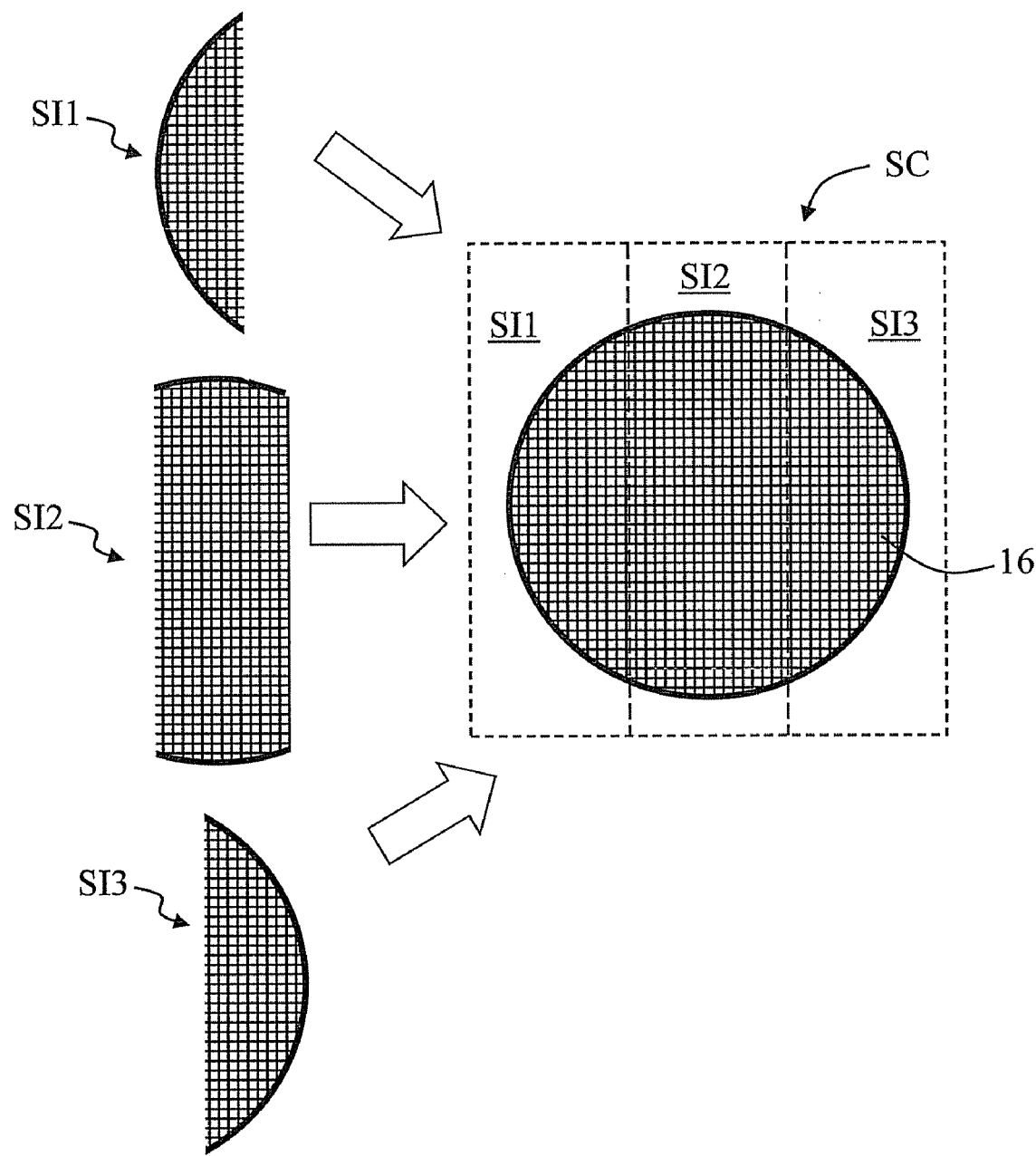
FIG. 9 is a schematic diagram that shows an example of how three scanned images are combined to form a composite image of the ceramic honeycomb structure endface.

FIG. 9 is a schematic diagram that shows three scanned images SI1, SI2 and SI3 combined to form a composite image SC of endface 16. Composite image SC is stored in controller 150 in memory unit 154. A typical size of composite image SC is about 2 gigabytes (32K×32K×2). In an example configuration of system 100 based on current technology, the process of scanning endface 16 to obtain composite image SC takes about 3 minutes.

Image Processing

Once composite image SC is obtained, it is then processed and analyzed by processor unit 152 using the aforementioned image processing software.

Since illumination non-uniformities can adversely affect the imaging quality and subsequent image processing and analysis, in a preliminary step any variation in the illumination provided by illuminator 140 is corrected. This is accomplished by scanning a white object that provides a uniform reflection. With uniform illumination, each pixel records the same image intensity. However, with non-uniform illumination, the pixels record the variation in intensity. This intensity variation is converted into a pixel weighting that can be used to compensate for any illumination non-uniformity. This pixel weighting is applied to the raw composite image SC to obtain a corrected composite image SC'.

Figure 10:
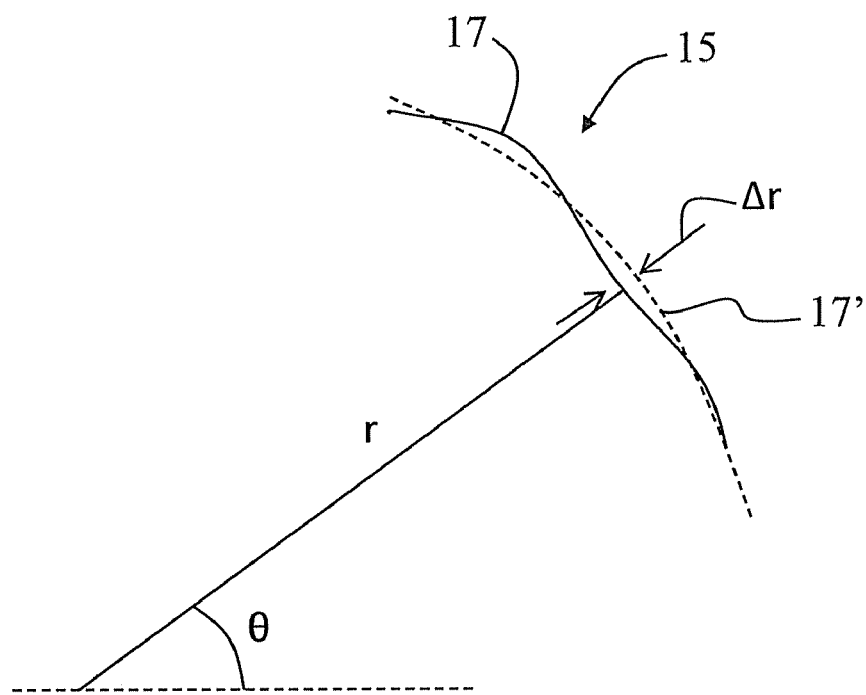
FIG. 10 is a schematic diagram that shows a portion of a perimeter of the composite image illustrating the relevant parameters for forming the shape vector.

The first main step in the image processing and analysis involves establishing "outside" parameters for the imaged ceramic honeycomb structure 10. Thus, in a first step the image processing is directed to find the perimeter 17 of endface 16 in corrected composite image SC'. FIG. 10 is a schematic diagram that shows a portion of a perimeter 17 of corrected composite image SC. Perimeter 17 is located by looking for the edge or outer skin 15. A best-fit shape (e.g., a circle, oval, etc.) is then fit to perimeter 17 to define a "best fit" perimeter 17' that also defines the geometric center of endface 16. A "shape vector" SV(θ, Δr) defines in polar coordinates the deviation from the actual perimeter shape 17 to the fitted perimeter shape 17'.

Figure 11:
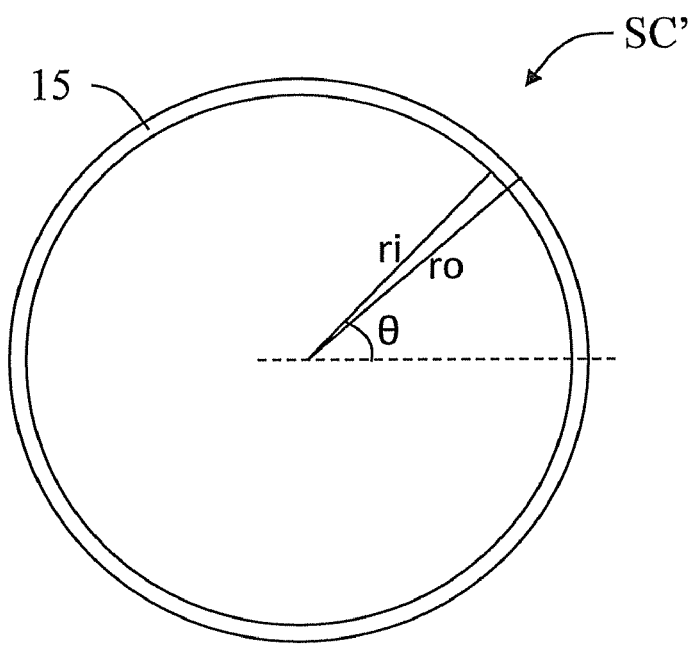
FIG. 11 is a schematic diagram that shows a portion of a perimeter of the composite image illustrating the relevant parameters for forming the thickness vector.

With reference to the schematic diagram of FIG. 11, the next step is to establish the variation in thickness of outer skin 15. This involves defining a "thickness vector" TH(θ, Δth), which is formed by measuring in the corrected composite image SC' the variation in skin thickness Δth=ro−ri, where ro is the outer skin radius and ri is the inner skin radius at angle θ.

The second main step in the image processing and analysis is to establish the "inside" parameters associated with web 19. This includes digitally removing outer skin 15 so that just web 19 of the corrected composite image SC' remains.

Figure 12A:
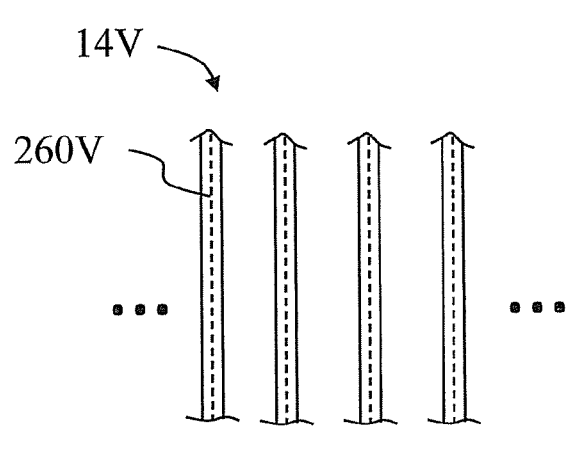
FIG. 12A and FIG. 12B respectively show horizontal and vertical portions of the web, along with corresponding horizontal and vertical centerlines determined by image processing.
Figure 12B:
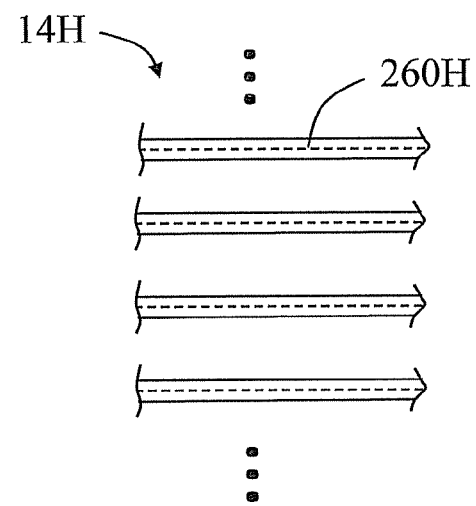

With reference to FIG. 12A and FIG. 12B, the next step is to start from the center of endface 16 as defined by the best-fit perimeter shape to find the vertically and horizontally oriented web walls 14 (respectively labeled 14V and 14H) in web 19. Vertical and horizontal centerlines 260V and 260H for vertical and horizontal web walls 14V and 14H are then established using, for example, a center-finding algorithm.

Figure 12C:
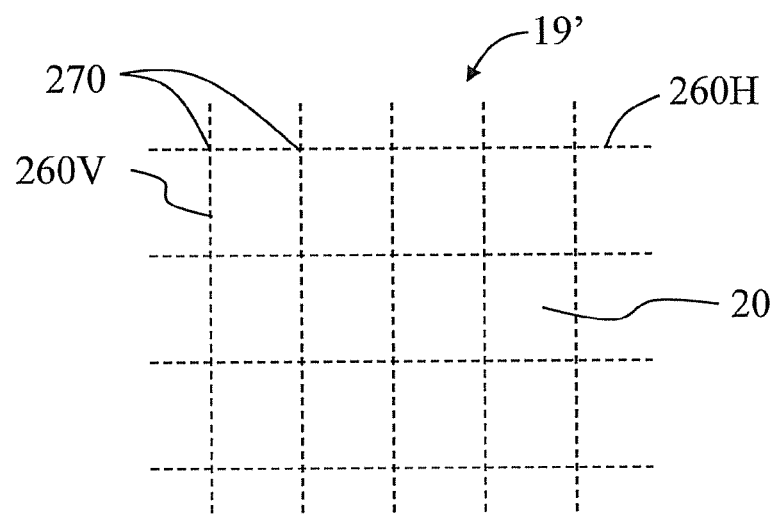
FIG. 12C shows the the best-fit vertical and horizontal centerlines superimposed to form an idealized web that includes best-fit web intersections that represent the "corners" of corresponding idealized cells.
Figure 13A:
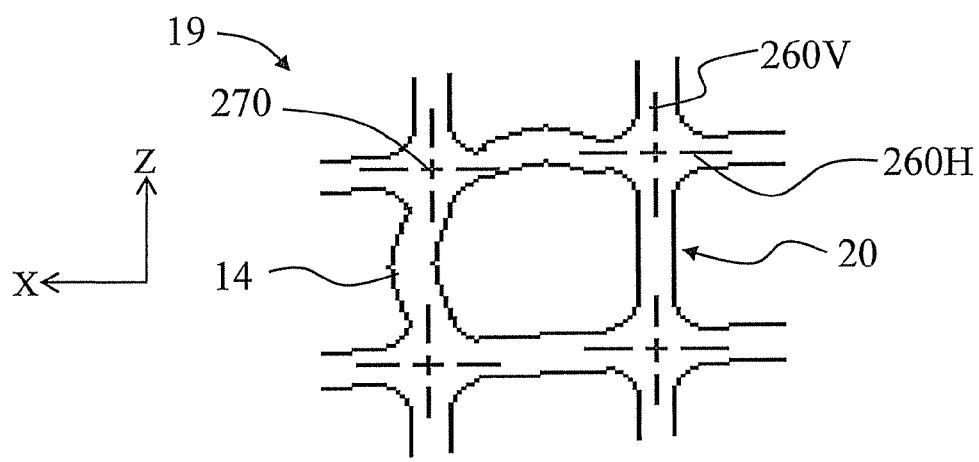
FIG. 13A depicts an example image of a cell in the composite image, along with the web intersections (cell corners)

With reference to FIG. 12C, the best-fit vertical and horizontal centerlines 260V and 260H are combined (superimposed) to form an idealized or reference web 19' that includes best-fit web intersections 270 that represent the "corners" of corresponding idealized cells 20'. FIG. 13A depicts an example image of a cell 20 in corrected composite image SC' along with the web intersections (cell corners) 270.

At this point, the next steps are directed to defining a number of parameters (e.g., wall thickness, wall angles, cell width, etc.) that describe the characteristics of each cell 20 by applying the reference web 19' to corrected composite image SC'. These parameters are collected in a "cell feature vector" $C_{ij}$, where i, j denote a given cell 20 in the matrix of cells making up web 19. For certain ceramic honeycomb structures 10 there are anywhere from 4000 to 10,000 cells 20 so that cell feature vector $C_{ij}$ can contain between 4000 to 10,000 elements.

Figure 13B:
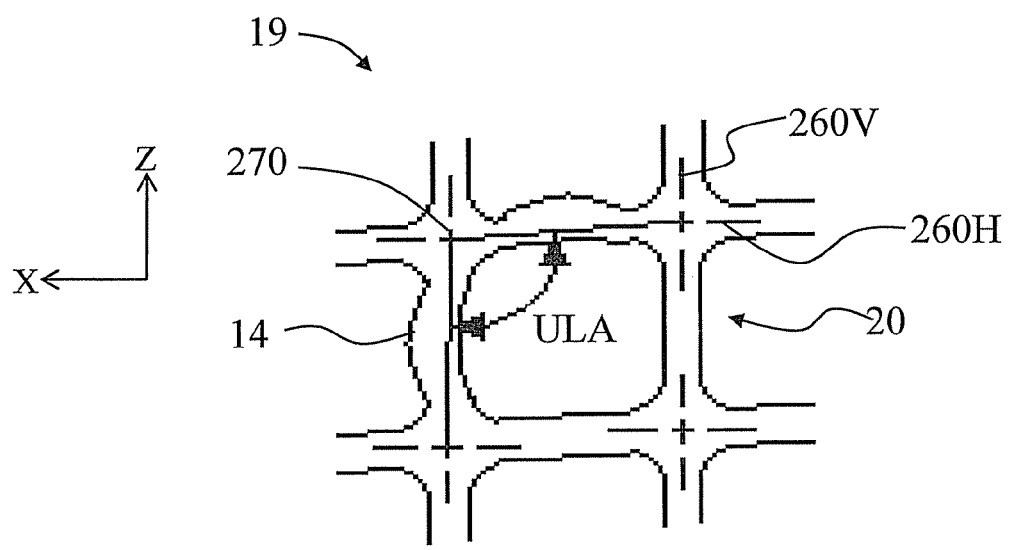
FIG. 13B is similar to FIG. 13A and shows a measure of the upper left angle of the cell.

FIG. 13B is similar to FIG. 13A and shows a measure of an angular parameter in the form of an "upper left angle" ULA of cell 20. While information concerning all four of the cell angles is available, only one cell angle per cell is needed to characterize the angular information for a given cell. Note that square cell 20 contains four angles so that all of the angles must add up to 360 degrees. Typically, the angles at the opposite corners of cell 20 are equal and the other two angles are approximate complementary angles, thereby allowing for just one cell angle for cell characterization.

Figure 13C:
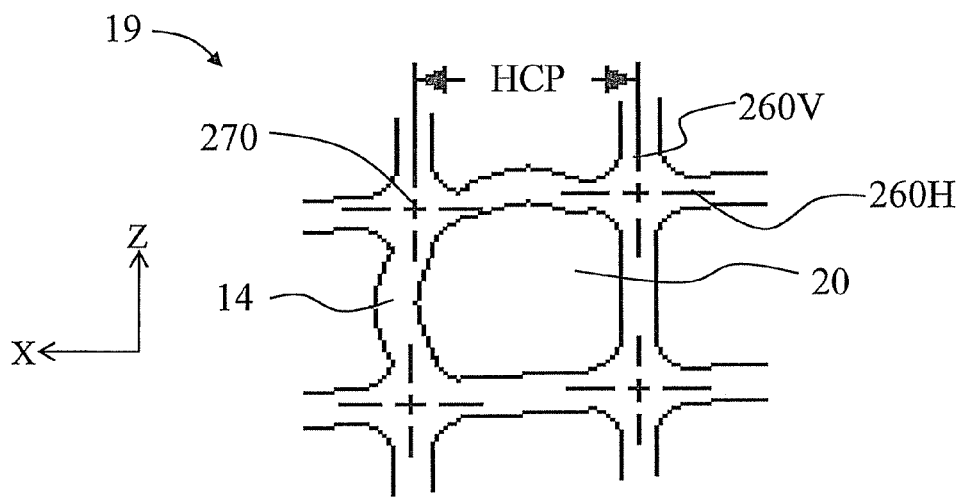
FIG. 13C is similar to FIG. 13B and illustrates the measurement of the horizontal cell pitch.

FIG. 13C is similar to FIG. 13B and illustrates the measurement of a parameter called the "horizontal cell pitch" HCP, which is measures the difference in the X-coordinates of cell corners 270. While each cell 20 includes two such cell pitches (upper and lower), only one such measurement is needed for most applications. In an example embodiment, an average of the upper and lower horizontal cell pitch HCP is used. Note also that the bottom HCP is the same as the top HCP of the cell directly below so that no information is lost.

Figure 13D:
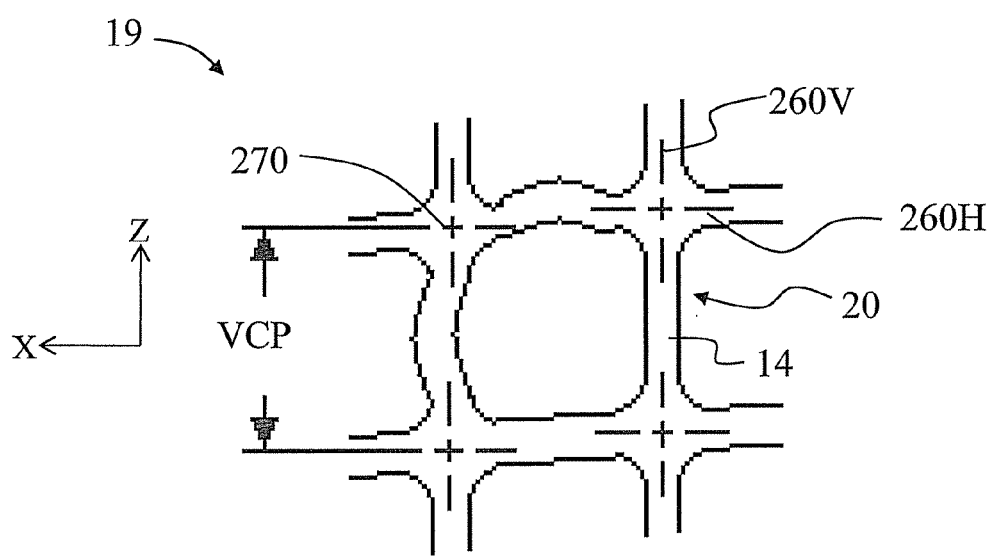
FIG. 13D is similar to FIG. 13C and illustrates the measurement of a the vertical cell pitch.

FIG. 13D is similar to FIG. 13C and illustrates the measurement of a related parameter called the "vertical cell pitch" VCP, which measures the difference in the Y-coordinates of cell corners 270. As is the case with the horizontal cell pitch HCP, while each cell includes two vertical cell pitches (upper and lower), only one such measurement is needed for most applications. In an example embodiment, an average of the left and right vertical cell pitch VCP is used. Note also that the right VCP is the same as the left HCP of the cell directly to the right so that no information is lost.

Figure 13E:
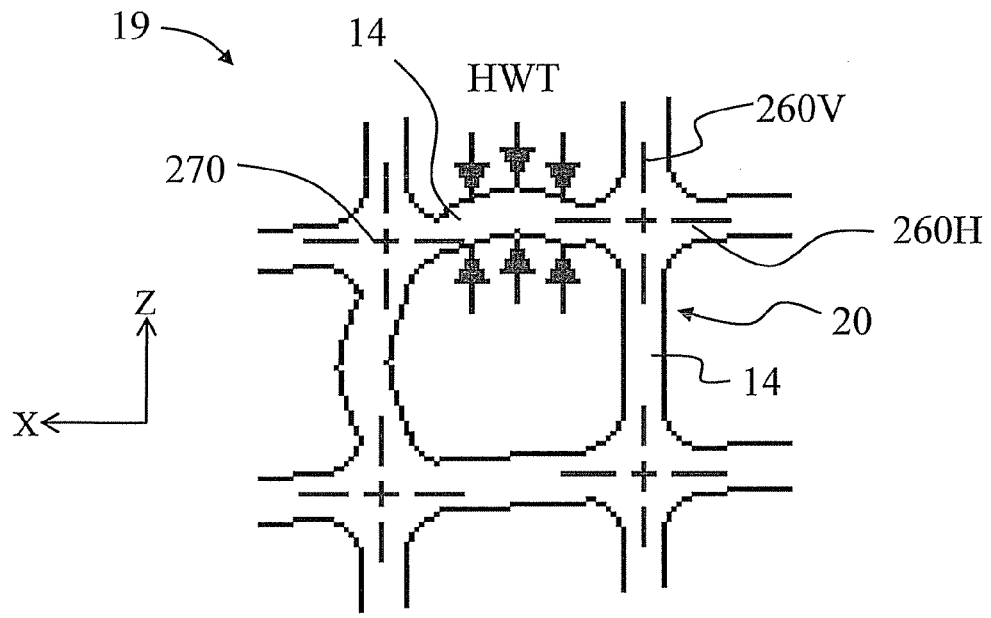
FIG. 13E is similar to FIG. 13D and illustrates the measurement of the horizontal wall thickness.

FIG. 13E is similar to FIG. 13D and illustrates the measurement of a parameter called the horizontal wall thickness HWT, which measures the location of the top and bottom edges of the top horizontal web wall 14 and subtracting the two locations. An example of this calculation is carried out for each set of 5 μm pixels that compose the top and bottom edges of web wall 14. Once the differences are calculated (this may produce between 100 and 300 thickness measurements, depending on the size of cell 20), they are averaged to produce an average thickness. In an example embodiment, the minimum thickness and maximum thickness are also stored in cell feature vector $C_{ij}$.

Figure 13F:
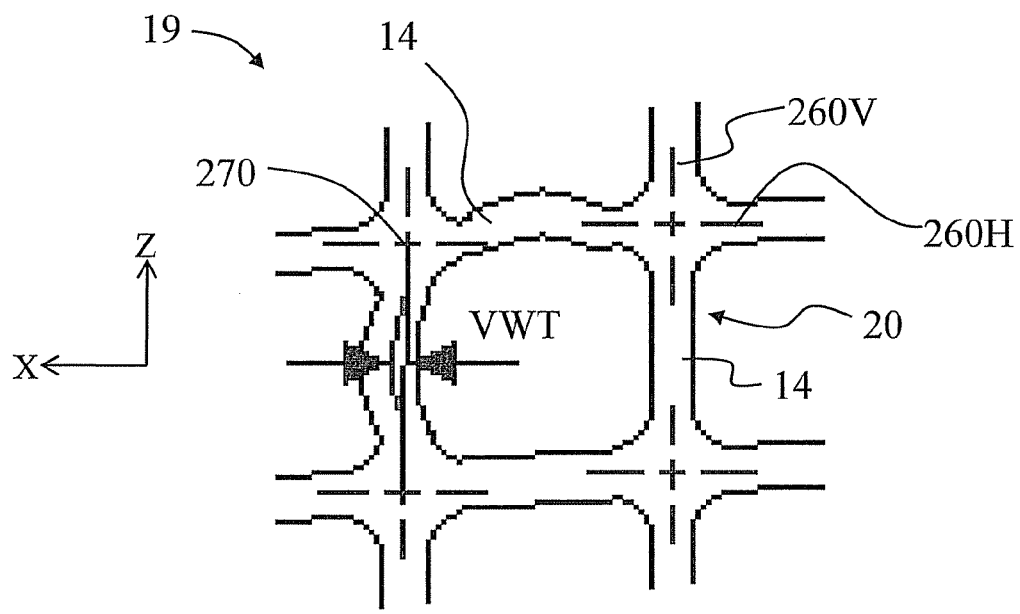
FIG. 13F is similar to FIG. 13E and illustrates the measurement of the vertical wall thickness.

FIG. 13F is similar to FIG. 13E and illustrates the measurement of a related parameter called the vertical wall thickness VWT, which is calculated in an analogous manner to the horizontal wall thickness HWT.

Figure 13G:
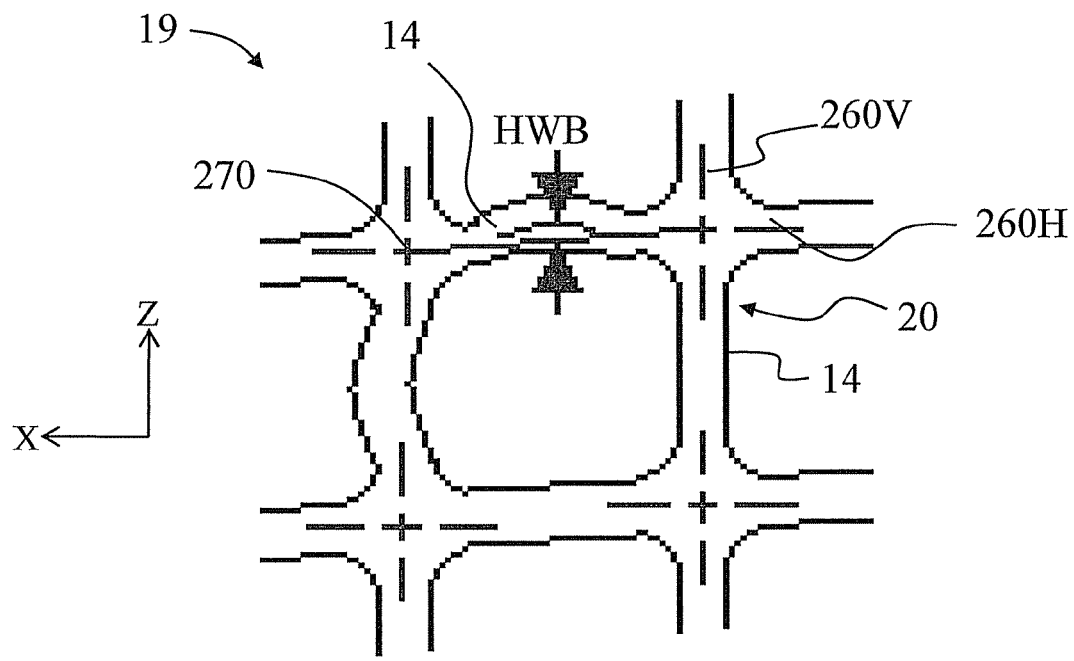
FIG. 13G is similar to FIG. 13F and illustrates the measurement of the horizontal wall bow.

FIG. 13G is similar to FIG. 13F and illustrates the measurement of a parameter called the horizontal wall bow HWB, which measures the center point of the top horizontal web wall 14. This center point is defined as the midway point between the two top corners 270 of the cell 20 and the midway point of the top of the web wall and the bottom of the web wall at the location of the midway point. A second point is found by drawing a line between the two top corner points of the cell and finding the center point of this line. The horizontal wall bow HWB is the difference in the X-direction between these two points. The web wall 14 can bow into the cell or away from the cell. If the bow projects into the cell its value is negative, and if it projects out from the cell it is positive.

Figure 13H:
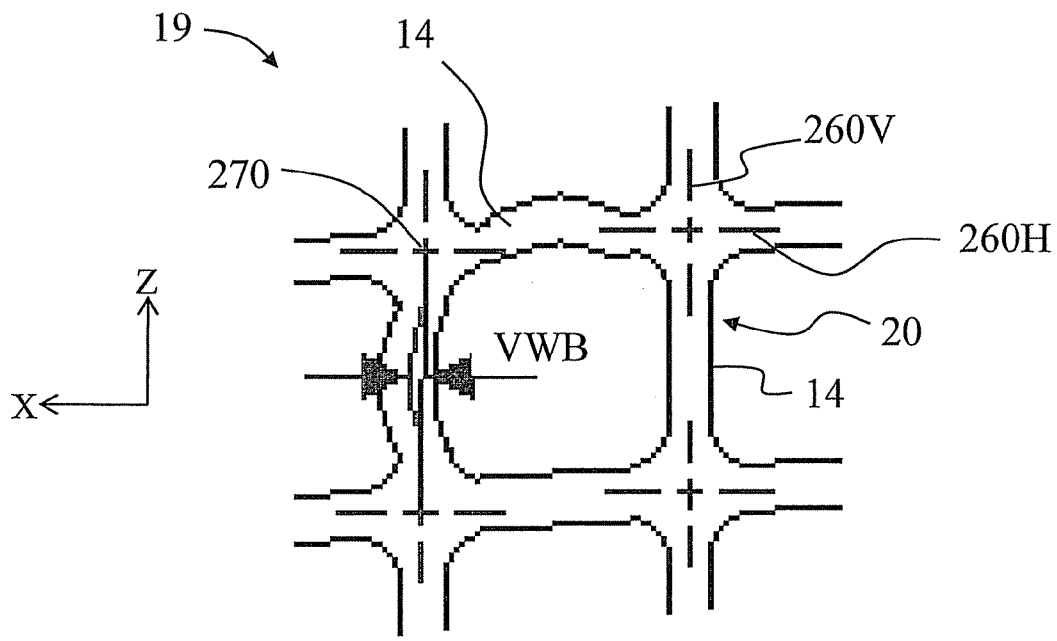
FIG. 13H is similar to FIG. 13G and illustrates the measurement of the vertical wall bow.

FIG. 13H is similar to FIG. 13G and illustrates the measurement of a related parameter called the vertical wall bow VWB, which is calculated in an analogous manner to the horizontal wall bow HWB.

Figure 14A:
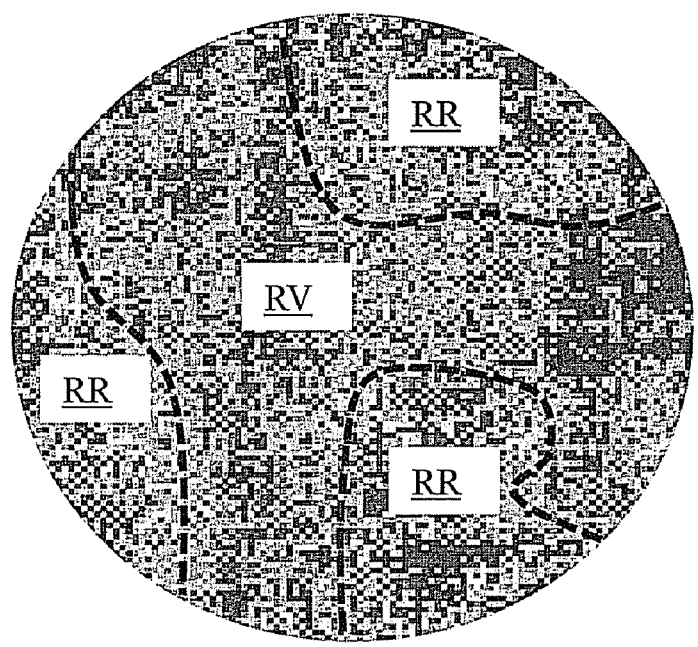
FIG. 14A is an example gray-scale attribute map based on a color attribute map that can be displayed on the display of high-resolution large-field scanning system.
Figure 14B:
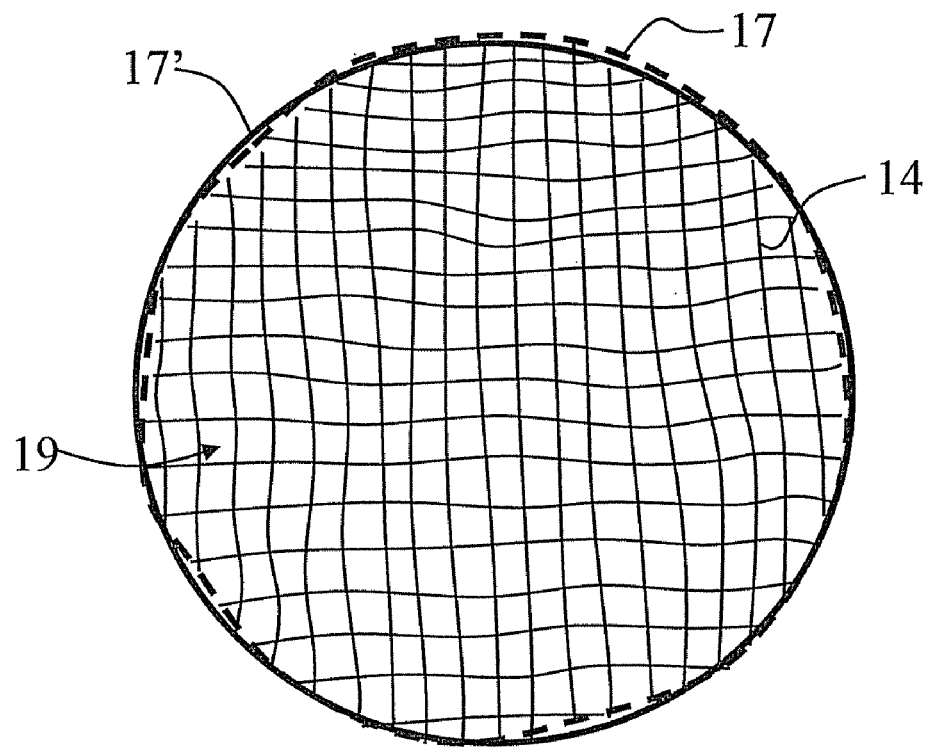
FIG. 14B is an example swell-o-gram that can be displayed on the display of high-resolution large-field scanning system.

The "inside" parameters ULA, HCP, VCP, HWT, VWT, HWB and VWB are stored in cell feature vector $C_{ij}$ in memory unit 154 (e.g., in a data file). Processor unit 152 is configured to search this vector and generate information, including visual representations of the information in the form of graphs, tabular reports, pictures, plots, charts, etc., which in an example embodiment is/are displayed on display 170. Two example visual representations of information include attribute maps and a swell-o-grams, which are shown in FIG. 14A and FIG. 14B, respectively. The "outside" parameters can also be analyzed and graphed in similar fashion, and both the inside and outside parameters can be combined and displayed on system display 170.

The attribute map of FIG. 14A maps of the variation in the upper left angle UAL of each cell 20. An ideal angle is 90°. The attribute map is shown in gray scale to illustrate the general principle and is based on a color map that follows the colors of the spectrum, with violet being the smallest angle and red denoting the largest angles. The regions RR denoted in the map by dashed lines have a generally "red" composition while the region RV has a generally "violet" composition. The color version of the map more clearly shows the trends and details of the spatial variation of upper left angle UAL. Attribute maps can be generated for any cell parameter. Processor unit 152 is programmed via the aforementioned image processing and analysis software to search cell feature vector $C_{ij}$ and pull out the row and column number of the particular parameter for each cell and plot it in a row and column map. The plotted map has the same spatial positioning as corrected composite image SC'.

The swell-o-gram of FIG. 14B is an example plot of the shape vector VS for endface 16. The actual perimeter 17 is also shown, along with a best-fit circular perimeter 17'. An example swell-o-gram plots only some of the web walls 14 (e.g., every fifth web wall) so that the general shape trends over web 19 are more easily observed. Example swell-o-grams also include a multiplication factor of the difference between ideal and actual values for the given parameter so that the distortion is more visible. Example multiplication factors range between 5× and 10×. In an example embodiment, multiple swell-o-grams for multiple ceramic honeycomb structures 10 are created and the results compared to identify any defect trends.

In other example embodiments, processor unit 152 is used to examine sub-groups of cells 20 in cell feature vector Cij to examine local trends, variations and effects. Using current technology, the total time for processing and analyzing corrected image SC' to generate the above information takes about 1 minute.

The measurements made by system 100 are additive with no accumulative error. Consider, for example, the case where measurements of the cell pitch in a row of cells are added together to produce a measurement of the length of the row of cells. The result is the exact size of the actual row plus/minus about 5 μm. This is because line-scan image sensor 124 sees all of the cells at once, and if one cell pitch measures a little bit bigger than expected, then the one next to it will measure a little bit smaller than expected. This is not always true for a microscopic-based inspection system. When such a system is used to measure the pitch of a cell, its measurements can be skewed slightly towards the high side or the low side. If this same measurement were completed for a hundred measurements taken on a the same row of cells mentioned above, and the resultant measurements were added, the result could be larger or smaller by approximately 100 times the error of the original cell pitch.

In an example embodiment, scanned images are taken and stored in memory unit 154 and then transferred to an external memory unit (e.g., a network storage device, not shown), where the scanned images are analyzed in batch mode by one or more powerful computers. This approach allows for making hundreds of measurements for each cell as well as processing the shape and thickness vectors. In another example embodiment, memory unit 154 and processor unit 152 are external to controller 150 and are part of a separate computer.

While the disclosure has been described with respect to several preferred embodiments, various modifications and additions will become evident to persons of skill in the art. All such additions, variations and modifications are encompassed within the scope of the disclosure, which is limited only by the appended claims, and equivalents thereto.

What is claimed is:

1. An inspection system for inspecting cells of a cellular ceramic substrate having an endface, comprising:
   an illuminator configured to provide normal-incidence line illumination on the endface over a plurality of cells;
   a movable stage that movably supports the ceramic structure so that the line illumination scans over the endface over a scan path;
   an optical imaging system having an axis and configured to form a line image of the illuminated plurality of cells;
   a line-scan image sensor arranged to receive and detect the line image and generate therefrom corresponding line-image signals; and
   a controller configured to process the line-image signals to form a composite image of the endface and determine therefrom at least one parameter of at least one cell.

2. The system of claim 1, wherein the illuminator includes a mirror arranged along the optical imaging system axis between the optical imaging system and the endface, the mirror configured to reflect an illumination beam along the axis to form the normal-incident line illumination.

3. The system of claim 1, wherein the optical imaging system is double-telecentric and has a magnification of 1×.

4. The system of claim 1, wherein the line image sensor includes at least about 8,000 square pixels having sides of less than or equal to about 5 μm.

5. The system of claim 1, wherein the optical imaging system has a depth of focus and the movable stage is configured to support the ceramic honeycomb body so that the endface remains within the depth of focus.

6. The system of claim 1, wherein the movable stage moves the honeycomb ceramic structure at a scan speed and the line-scan image sensor has a scan rate and includes an encoder that couples the scan rate to the scan speed.

7. The system of claim 1, wherein the controller includes a memory unit adapted to store line images, and includes a processor unit adapted to process line images to form the composite image and to process the composite image to determine said at least one parameter.

8. A method of inspecting cells at an endface of a cellular ceramic substrate, comprising:
capturing along an optical axis line images of illuminated cells as a line illumination scans over at least a portion of the plurality of cells, including centering the line illumination on the optical axis to make the line illumination normally incident upon the endface;
forming from the line images a composite image of the cells; and
determining from the composite image at least one parameter of at least one cell.

9. The method of claim 8, further comprising determining a plurality of cell parameters for each of a plurality of cells.

10. The method of claim 8, further comprising selecting the at least one cell parameter from the group of cell parameters comprising: cell corner angle, horizontal cell pitch, vertical cell pitch, horizontal wall thickness, vertical wall thickness, horizontal wall bow and vertical wall bow.

11. The method of claim 8, wherein the cellular ceramic substrate includes an outer skin, the composite image includes an image of the outer skin, the method further comprising determining from the composite image at least of an outer skin thickness variation and an outer skin shape variation.

12. The method of claim 8, further comprising moving the ceramic substrate while keeping the line illumination stationary.

13. The method of claim 8, further comprising forming the digital line images so that digital line images taken over adjacent scan paths partially overlap.

14. The method of claim 8, further comprising forming a reference web and performing said determining of said at least one cell parameter based on the reference web.

15. The method of claim 8, further comprising displaying information based on the at least one cell parameter.

16. A method of inspecting a honeycomb cellular ceramic substrate having an endface, an array of cells and an outer skin, comprising:
normally illuminating and digitally imaging at least a portion of the array of cells while moving the cellular ceramic structure to obtain a scanned image of said portion of the array of cells; and
processing the scanned image to determine at least one parameter of at least one cell.

17. The method of claim 16, further comprising forming the illuminating of the portion of the array of cells as an elongate line-type portion.

18. The method of claim 16, further comprising forming the scanned image as a composite of scanned images taken over different scan path segments.

19. The method of claim 16, further comprising forming a reference web from the scanned image and determining the at least one parameter from the reference web.

20. The method of claim 19, wherein the scanned image includes an image of the outer skin, the method further comprising determining at least one of an outer skin thickness and an outer skin shape.

* * * * *